US006391546B1

(12) United States Patent
Karube et al.

(10) Patent No.: US 6,391,546 B1
(45) Date of Patent: May 21, 2002

(54) METHOD FOR DETECTING TARGET NUCLEOTIDE SEQUENCE (75) Inventors: Isao Karube, 1-3-16, Higashi-Arima, Miyamae-Ku, Kawasaki-Shi, Kanagawa-Ken; Shinya Sawata, Tsuchiura; Ryohei Nagata, Tokyo-To, all of (JP)

(73) Assignees: Isao Karube, Kawasaki; Dai Nippon Printing Co., Ltd., Tokyo-To, both of (JP)

( * ) Notice: Subject to any disclaimer, the term of this patent is extended or adjusted under 35 U.S.C. 154(b) by 0 days.

(21) Appl. No.: 09/147,251

(22) PCT Filed: May 8, 1998

(86) PCT No.: PCT/JP98/02039

§ 371 Date: Nov. 12, 1998

§ 102(e) Date: Nov. 12, 1998

(87) PCT Pub. No.: WO98/50581

PCT Pub. Date: Nov. 12, 1998

(30) Foreign Application Priority Data

May 8, 1997 (JP) .............................................. 9/117725
Mar. 23, 1998 (JP) ............................................ 10/074442
May 6, 1998 (JP) ............................................ 10/123371

(51) Int. Cl.[7] .................................................. C12Q 1/68
(52) U.S. Cl. ........................ 435/6; 435/91.1; 536/24.3; 536/24.31; 536/23.1; 536/25.4; 935/80
(58) Field of Search .................... 435/6, 91.1; 536/24.3, 536/24.31, 23.1, 25.4; 935/80

(56) References Cited

U.S. PATENT DOCUMENTS

| 5,030,557 | A | | 7/1991 | Hogan et al. |
| 5,464,743 | A | | 11/1995 | Weisburg et al. |
| 5,474,895 | A | | 12/1995 | Ishii et al. |
| 5,485,277 | A | * | 1/1996 | Foster ......................... 356/445 |
| 5,637,685 | A | * | 6/1997 | Soares et al. .............. 536/23.1 |
| 5,695,926 | A | | 12/1997 | Cros et al. |
| 5,753,439 | A | * | 5/1998 | Smith et al. .................... 435/6 |
| 6,007,987 | A | * | 12/1999 | Canto et al. .................... 435/6 |

FOREIGN PATENT DOCUMENTS

| EP | 0 622 464 | 11/1994 |
| JP | 6-30797 | 2/1984 |
| JP | 4-320700 | 11/1992 |
| JP | 5-503215 | 6/1993 |
| JP | 5-252998 | 10/1993 |
| JP | 7-174693 | 7/1995 |
| WO | WO 91/13174 | 9/1991 |

* cited by examiner

*Primary Examiner*—W. Gary Jones
*Assistant Examiner*—Janell E. Taylor
(74) *Attorney, Agent, or Firm*—Oblon, Spivak, McClelland, Maier & Neustadt, P.C.

(57) ABSTRACT

An object of the present invention is to provide a method for detecting a target nucleotide sequence using a complementary nucleotide sequence that has an excellent sensitivity of detection. The method comprises the steps of converting the target nucleotide sequence to a partially double-stranded nucleotide sequence which is double-stranded at one part and single-stranded in the remaining part and detecting said partially double stranded nucleotide sequence using a nucleotide sequence that is complementary to the target nucleotide sequence.

13 Claims, 6 Drawing Sheets

```
          10         20         30         40         50         60
ATGAAGTGTA TATTATTTAA ATGGGTACTG TGCCTGTTAC TGGGTTTTTC TTCGGTATCC 70         80         90        100        110        120
TATTCCCGGG AGTTTACGAT AGACTTTTCG ACCCAACAAA GTTATGTCTC TTCGTTAAAT 130        140        150        160        170        180
AGTATACGGA CAGAGATATC GACCCCTCTT GAACATATAT CTCAGGGGAC CACATCGGTG 190        200        210        220        230        240
TCTGTTATTA ACCACACCCC ACCGGGCAGT TATTTTGCTG TGGATATACG AGGGCTTGAT 250        260        270        280        290        300
GTCTATCAGG CGCGTTTTGA CCATCTTCGT CTGATTATTG AGCAAAATAA TTTATATGTG 310        320        330        340        350        360
GCCGGGTTCG TTAATACGGC AACAAATACT TTCTACCGTT TTTCAGATTT TACACATATA
  P-VT2C 370        380        390        400        410        420
TCAGTGCCCG GTGTGACAAC GGTTTCCATG ACAACGGACA GCAGTTATAC CACTCTGCAA
                       asp-VT-2a            antiprobe VT2-2B 430        440        450        460        470        480
CGTGTCGCAG CGCTGGAACG TTCCGGAATG CAAATCAGTC GTCACTCACT GGTTTCATCA
  asp-VT-2b 490        500        510        520        530        540
TATCTGGCGT TAATGGAGTT CAGTGGTAAT ACAATGACCA GAGATGCATC CAGAGCAGTT
```

METHOD FOR DETECTING TARGET NUCLEOTIDE SEQUENCE

BACKGROUND OF THE INVENTION

1. Field of the Invention

The present invention relates to a method for detecting a target nucleotide sequence using a complementary nucleotide sequence.

2. Background Art

A number of methods for detecting a target deoxyribonucleic acid (DNA) using a DNA that is complementary to the DNA sequence ("complementary DNA") are well known. A typical example is the Southern blotting method to identify a specified DNA. Plaque hybridization and colony hybridization used in DNA cloning are also well known technique. The target DNA has first to be separated into a single strand as these methods are based on the fact that a target DNA hybridizes specifically to its complementary DNA.

However, with the exception of the Southern blotting method in which it is immobilized on a membrane, a single-strand DNA becomes spherical and such spherical DNA can not hybridize with the complementary DNA. Furthermore, it is necessary to heat a double-stranded DNA in order to convert it to a single-strand DNA. However such treatments adversely affect the target DNA.

SUMMARY OF THE INVENTION

The inventors found that the sensitivity of detecting a target nucleotide sequence using a complementary nucleotide sequence is remarkably improved by converting the target nucleotide sequence into a partially double-stranded nucleotide sequence. The present invention is based on this finding.

An object of the present invention is to provide a method of detecting a target nucleotide sequence using a complementary nucleotide sequence that has an excellent sensitivity of detection.

Another object of the present invention is to provide a method of producing a partially double-stranded nucleotide sequence that is used for the method of detecting the target nucleotide sequence.

The method of detecting a target nucleotide sequence according to the present invention comprises the steps of converting a target nucleotide sequence into a partially double-stranded nucleotide sequence and detecting the partially double-stranded nucleotide sequence using a complementary nucleotide sequence to the target nucleotide sequence ("complementary nucleotide sequence").

DETAILED DESCRIPTION OF THE INVENTION

The term "partially double-stranded nucleotide sequence" as used herein refers to a nucleotide sequence which has a double-stranded portion and a single-stranded portion. The single-stranded portion of this "partially double-stranded nucleotide sequence" should have sufficient length to hybridize the complementary nucleotide sequence. Accordingly, the term "partially double-stranded nucleotide sequence" herein generally means a nucleotide sequence which has 6 or more bases of the single-stranded portion.

The term "nucleotide sequence" as used herein refers to DNA and RNA.

The expression "to convert to a partially double-stranded nucleotide sequence" refers not only to simple process for making a partially double-stranded nucleotide sequence from a target nucleotide sequence but also to amplification process of the target nucleotide sequence by the polymerase chain reaction (PCR) method to make a partially double-stranded nucleotide sequence.

Examples of the target nucleotide sequence include DNA coding for verotoxin of pathogenic *Escherichia coli*, DNA coding for gp120 (the coating protein of HIV), specific nucleotide sequences (cDNA) of 16SrRNAs of various microorganisms, and a DNA coding for the antibiotic binding protein of methicillin-resistant staphylococcus (MRSA). The target nucleotide sequence may contain impurities. For example, a heat-treated pathogenic *E. coli* preparation can be used without further purification as a test sample in detecting the DNA coding for verotoxin of pathogenic *E. coli*.

A method for converting a target nucleotide sequence into a partially double-stranded nucleotide sequence, namely the method for producing a partially double-stranded nucleotide sequence according to the present invention, includes the following steps of:

(1) performing an asymmetric polymerase chain reaction in which the target nucleotide sequence is used as a template, and an oligonucleotide having a nucleotide sequence identical to a part of the target nucleotide sequence (primer 1) and an oligonucleotide having a nucleotide sequence complementary to a part of the target nucleotide sequence (primer 2) are used as primers;

(2) performing an asymmetric polymerase chain reaction in which the target nucleotide sequence is used as a template, and primer 1 and an oligonucleotide having a nucleotide sequence complementary to a part of the target nucleotide sequence except for primer 2 (primer 3) are used as primers; and (3) obtaining a partially double-stranded nucleotide sequence by heating and cooling a mixture of the amplification products of step (1) and step (2).

The method for converting a target nucleotide sequence into a partially double-stranded nucleotide sequence may include the following steps (A) and (B) prior to step (1):

(A) synthesizing an oligonucleotide (primer 1) having a nucleotide sequence identical to a part of the target nucleotide sequence;

(B) synthesizing two oligonucleotides (primer 2 and primer 3) having a nucleotide sequence complementary to a part of the target nucleotide sequence.

Figure 1:
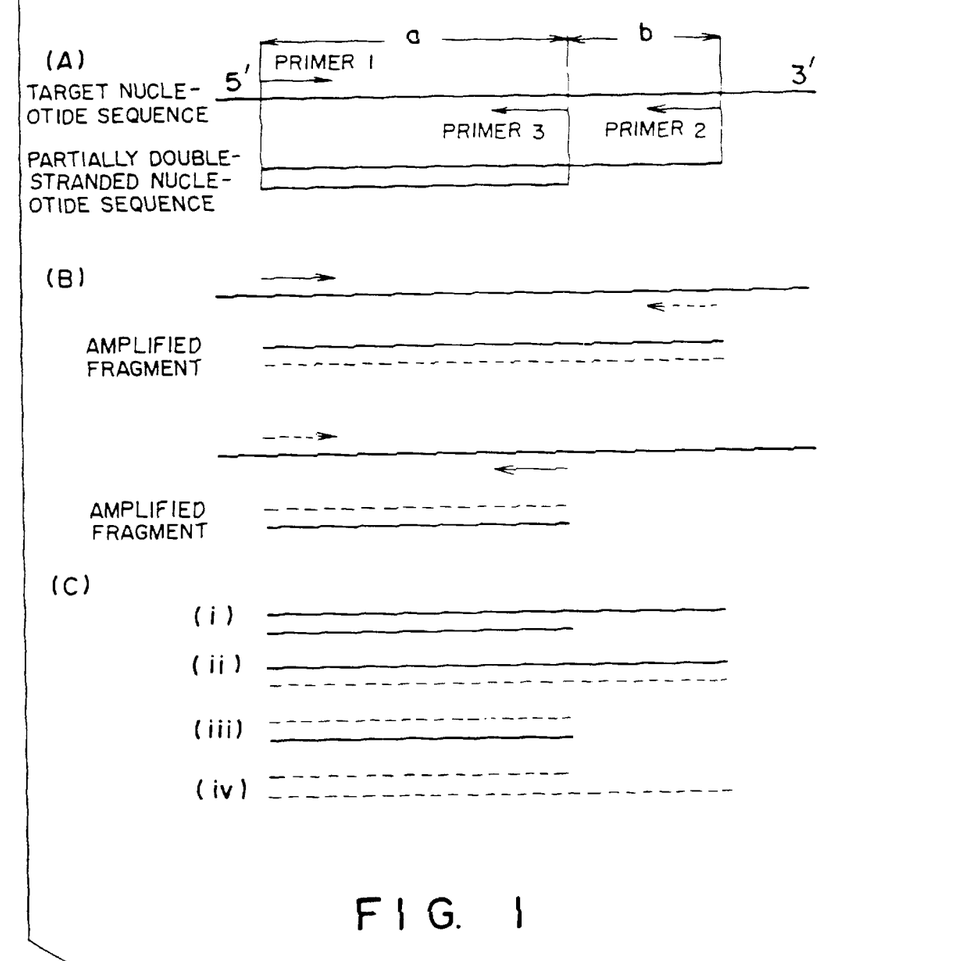
FIG. 1 schematically illustrates a method of producing a partially double-stranded nucleotide sequence using an asymmetrical PCR.

An example of the positions of primers 1, 2 and 3 on the target nucleotide sequence is shown in FIG. 1. Primer 1 can be located closer to the 5' end (namely upstream) by a distance a or a+b than primers 2 and 3. As shown in FIG. 1 (A), a and b correspond to a double-stranded part and a single-stranded part of the partially double-stranded nucleotide sequence, respectively. The length of a and b can be appropriately determined in accordance with the complementary nucleotide sequence to be used for detection. However, since a length of less than 84 bases causes problems such that excessive byproducts are produced during PCR, a is preferably 100 to 2000 bases long and b is preferably 85 to 1985 bases long.

In steps (1) and (2), an asymmetrical PCR is performed using the target nucleotide sequence as a template and primers 1 to 3 as primers. In the asymmetrical PCR, one of the two primers used in the PCR is provided in excess over the other primer (Gyllensten U. B. et al., Proc. Natl. Acad. Sci. USA, 85, 7652–7655 (1988)).

Each primer can be used in the asymmetrical PCR as follows. For example, as shown in FIG. 1 (B), primer 1 is provided in excess over primer 2 to obtain a long amplified fragment of the target nucleotide sequence while primer 3 is provided in excess over primer 1 to obtain a short amplified fragment, having a sequence that is complementary to the target nucleotide sequence. In FIG. 1, the solid arrow is the primer which is provided in an excessive amount and the broken arrow is the primer provided in a lesser amount. The primer provided in excess is preferably 10 to 100 times, more preferably 20 times, over the other primer. The temperature, time, cycle and other variables in the PCR can be determined in accordance with the nucleotide fragment to be amplified.

The PCR are performed twice under the conditions described above to obtain the amplified fragment as shown in FIG. 1 (B). In FIG. 1, the solid line shows an amplified fragment obtained in a large amount and the broken line shows the amplified fragment obtained in a small amount.

In step (3), the amplified products obtained in steps (1) and (2) are mixed, heated and cooled to obtain a partially double-stranded nucleotide sequence. Heating is preferably carried out for 5 to 10 minutes at 90 to 95° C. and cooling is preferably carried out over a period of 20 to 30 minutes to cool the product to 18 to 30° C. After these mixing, heating and cooling processes, four kinds of nucleotide fragments, (i), (ii), (iii) and (iv) as shown in FIG. 1 (C), are obtained. Only nucleotide fragment (i) is obtained in a large amount and the other three nucleotide fragments are obtained in small amounts. The single-stranded part of the partially double-stranded nucleotide sequence in (i) consists of a part of the target nucleotide sequence.

Figure 2:
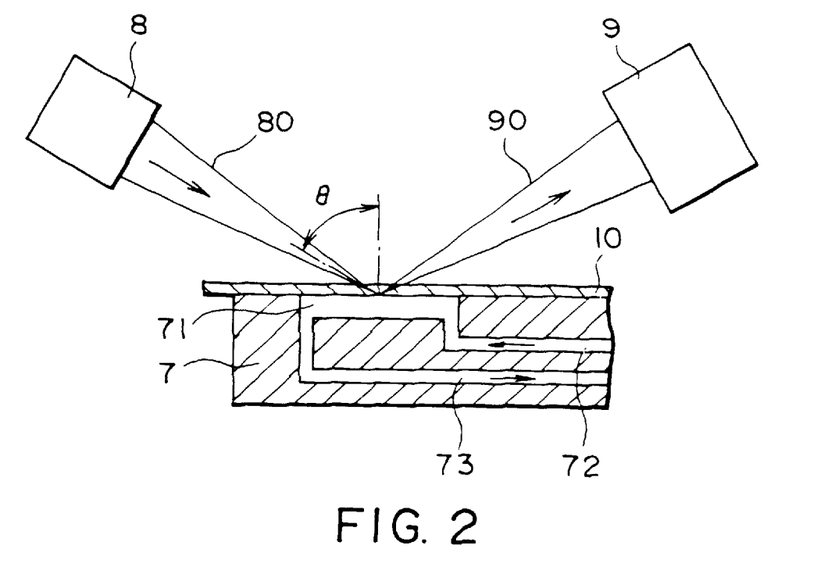
FIG. 2 shows an example of a surface plasmon resonance biosensor. 7: cartridge block; 71: measuring cell; 72 and 73: passage; 8: light source; 80: incident light; 9: detector; 90: reflecting light; 10: measuring chip.

The partially double-stranded nucleotide sequence can be detected by a hybridization method using a nucleotide sequence complementary to the target nucleotide sequence (complementary nucleotide sequence). The complementary nucleotide sequence can be the nucleotide sequence that is complementary to the whole or a part of the single-stranded part of the partially double-stranded nucleotide sequence. Detection can be carried out using detectable labels such as radioisotopes (e.g., $^{32}$P), enzymes, enzyme substrates or fluorescence which are carried on the complementary nucleotide sequence. Detection by labeled probes can be carried out using conventional methods. Detection can also be carried out using a surface plasmon resonance biosensor. The surface plasmon resonance biosensor and measuring chips to be used for detecting a target nucleotide sequence will be explained as follows:

An example of a surface plasmon resonance biosensor used in the present invention is shown in FIG. 2. This surface plasmon resonance biosensor has a cartridge block 7, a light source 8 and a detector 9 and is used by placing a measuring chip 10 on which a complementary nucleotide sequence is immobilized. Chip 10 is provided on cartridge block 7. The upper side of cartridge block 7 has a hollow and a measuring cell 71 consists of this hollow and measuring chip 10. Measuring chip 71 is communicated with the outside of cartridge block 7 via passages 72 and 73. The sample flows into measuring cell 71 via passage 72 and is discharged after measurement via passage 73.

Monochromatic light (an incident light 80) is irradiated from light source 8 toward the transparent substrate of measuring chip 10. A reflected light 90 which is reflected by a metal membrane set on the reverse side of measuring chip 10 reaches detector 9 which can detect the intensity of reflected light 90.

The biosensor as shown in FIG. 2 yields a reflected light intensity curve which forms a trough relative to a given angle of incidence θ. The trough in the reflected light intensity curve is due to surface plasmon resonance. When light is totally reflected at the interface between the transparent substrate and the exterior of measuring chip 10, a surface wave known as an evanescent wave is generated at the interface and a surface wave known as a surface plasmon is also generated on the metal membrane. Resonance occurs when the wave number of these two surface waves coincides, and a part of light energy is consumed to excite the surface plasmon resulting in a decrease in the intensity of the reflected light. The wave number of the surface plasmon is affected by the refractive index of the medium proximate to the surface of the metal membrane. Therefore, when the refractive index of the medium changes due to an interaction between the nucleotide sequence to be detected and its complementary nucleotide sequence, a surface plasmon resonance is induced to change the angle of incidence θ. Thus, a change in the concentration of the nucleotide sequence to be detected can be perceived by a shift of the trough in the reflected light intensity curve. The change in the angle of incidence θ is called a resonance signal and a change of $10^{-4}$ degree is expressed as 1 RU.

Figure 3:
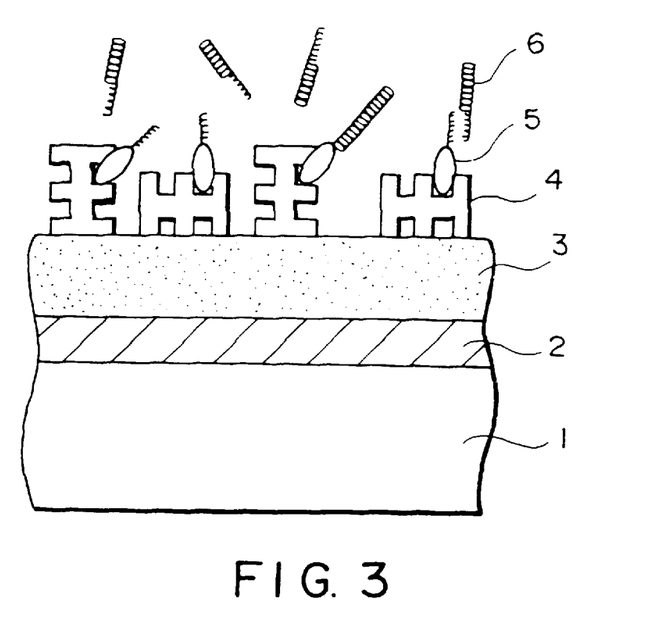
FIG. 3 shows an example of the measuring chip for the surface plasmon resonance biosensor. 1: transparent substrate; 2: metal membrane; 3: organic layer; 4: avidin; 5: biotin-labeled complementary nucleotide sequence; 6: partially double-stranded nucleotide sequence.

Measuring chip 10 may have a transparent substrate and a metal membrane necessary for surface plasmon resonance and a complementary nucleotide sequence can be immobilized on the metal membrane of the chip. Commercially available measuring chips (for example, a measuring chip for BIAcore 2000, Pharmacia Biosensor, Inc.) may be used. The measuring chip as shown in FIG. 3 is preferable. A metal membrane 2 and an organic layer 3 are molded onto a transparent substrate 1. Avidin 4 is immobilized on the organic layer, and a complementary nucleotide sequence labeled with biotin is immobilized on avidin 4.

Transparent substrate 1 is not particularly restricted, and can be any substrate used in a measuring chip for a surface plasmon resonance biosensor. Generally, substrates made of materials which are transparent to a laser beam, such as glass, poly(ethylene terephthalate) and polycarbonates can be used. A material which is not anisotropic to polarized light and which can be easily processed is desirable. The thickness of the substrate can be about 0.1 to 20 mm.

Metal membrane 2 is not particularly restricted provided it can induce surface plasmon resonance. Examples of the metal to be used for this metal membrane include gold, silver, copper, aluminum and platinum. They can be used alone or in combination. Furthermore, for better adhesion to the transparent substrate, an auxiliary layer may be set between transparent substrate 1 and the layer made of gold, silver or the like.

The thickness of metal membrane 2 is preferably 100 to 2000 angstroms, most preferably 200 to 600 angstroms. When the thickness exceeds 3000 angstroms, surface plasmon phenomena of the medium cannot be sufficiently detected. Furthermore, when an auxiliary layer made of chrome is used, the thickness of the layer is preferably 5 to 50 angstroms.

Metal membrane 2 can be formed by a conventional method such as sputtering, vacuum evaporation, ion plating, electroplating or non-electrolytic plating. The sputtering method is preferable.

Organic layer 3 consists of a substance which can bind both to a metal atom and to an avidin molecule. The thickness of the organic layer is preferably 10 to 200 angstroms, most preferably 10 to 50 angstroms. Furthermore, aside from an avidin-biotin bond, a nucleotide sequence can be immobilized on organic layer 3 using a covalent bond, such as an ester bond or amide bond.

The organic layer can be formed using a silane coupling agent or a compound having a mercapto group and another organic functional group ("thiol compound"), or using the LB (Langmuir-Blodgett's) technique. A membrane formed by the LB technique binds to the metal membrane weaker than a membrane formed using a silane coupling agent or a thiol compound. However, the LB technique is applicable to a wider range of substances and can form an agglomerated membrane. Therefore, the number of physiologically active substances to be bound per unit area can be increased.

Examples of silane coupling agents that can be used to form the organic layer include 3-aminopropyltriethoxysilane, 3-aminopropyltrimethoxysilane, 3-aminopropyldiethoxymethylsilane, 3-(2-aminoethylaminopropyl)trimethoxysilane, 3-(2-aminoethylaminopropyl)dimethoxymethylsilane, 3-mercaptopropyltrimethoxysilane and dimethoxy-3-mercaptopropylmethylsilane. Examples of thiol compounds include mercaptoaminomethane, 2-mercapto-1-aminoethane, 3-mercapto-1-aminopropane, 4-mercapto-1-aminobutane, 1,1,1-triamino-2-mercaptoethane, mercaptoacetic acid, 2-mercaptopropionic acid, 3-mercaptobutyric acid, 4-mercaptovaleric acid and 1,1,1-triamino-3-mercaptopropane. Multi-functional substances having many binding sites with avidin, such as 1,1,1-triamino-2-mercaptoethane and 1,1,1-triamino-3-mercaptopropane, are preferably used. Examples of substrates applicable to the LB technique include 21-aminodocosanoic acid, stearyl amine and polylysine.

Examples of methods for forming the organic layer by a silane coupling agent include the exposure of a metal membrane to saturated vapor of a silane coupling agent for a certain period of time (saturated vapor method), the immersion of a metal membrane into a solution containing a silane coupling agent (immersion method), a spin coater (spin coating method) and a photogravure press (gravure method). The saturated vapor method, immersion method, spin coating method or gravure method can be used to form organic layer 3 using a thiol compound.

Avidin 4 can be immobilized on organic layer 3 by contacting a fixed amount of avidin 4 with organic layer 3 for a fixed period of time. More specifically, transparent substrate 1 with adhered organic layer 3 is positioned on the flow cell type surface plasmon resonance biosensor and a fixed amount of avidin 4 is poured for a fixed period of time.

Examples of methods to immobilize a complementary nucleotide sequence labeled with biotin include the ink jet method and macro dispenser method. The ink jet method has an advantage in that it can precisely eject a drop containing a complementary nucleotide sequence 5 onto an extremely small area so that complementary nucleotide sequence 5 to be immobilized can be utilized efficiently. Immobilization can be carried out by positioning a measuring chip onto a flow cell type surface plasmon resonance biosensor and pouring a certain amount of complementary nucleotide sequence 5 for a fixed period of time. This immobilizing method has an advantage that immobilization of avidin 4 and complementary nucleotide sequence 5 can be done consecutively. One method of labeling the complementary nucleotide sequence with biotin is by PCR using a primer having biotin.

The target nucleotide sequence may be one or more. Two or more kinds of target nucleotide sequences can be detected by immobilizing multiple numbers of nucleotide sequences onto one chip or by providing multiple numbers of chips onto the sensor. Detection of two or more kinds of nucleotide sequences in this manner will provide better accuracy in detection of the nucleotide sequences. Whether a sample contains DNA derived from a certain microorganisms can be identified with high accuracy, for example, by immobilizing two or more DNA sequences complementary to specific DNA of said microorganism. Accuracy can be improved also by including a DNA sequence which does not bind to the target DNA (negative probe) in the DNA sequences being immobilized. Furthermore, by selectively immobilizing a nucleotide sequence, not only the presence or absence of verotoxin in the sample but also the type of toxin, type I or type II, can be determined.

When two or more target nucleotide sequences are immobilized, the surface plasmon resonance biosensor to be used is preferably of the type in which the measuring chip can freely move in the horizontal direction. Such sensor will enable the measurement of signals of multiple numbers of samples on the chip while leaving the optical system fixed.

EXAMPLE

Example 1

A 0.1% avidin solution was poured into the measuring cell of a commercial surface plasmon resonance biosensor (BIAcore 2000, Pharmacia Biosensor) at a flow rate of 5 $\mu$l/min for 10 minutes to immobilize avidin onto the measuring chip. An oligonucleotide which is complementary to the 401–421 base sequence of the DNA sequence (SEQ ID NO. 1) coding for type 2 verotoxin shown in FIG. 4 was synthesized and biotin was bound to its 5' end (this oligonucleotide is "antiprobe VT2-2B"). A solution containing antiprobe VT2-2B was poured into the measuring cell of the biosensor at a flow rate of 1 $\mu$l/min for 50 minutes to immobilize the oligonucleotide via avidin onto the measuring chip.

The following primers were synthesized based on the DNA sequence shown in FIG. 4:

```
p-VT2C        GCCGGGTTCGTTAATACGGCA
              (SEQ ID NO. 2)
asp-VT2-2a    CTGTCCGTTGTCATGGAAACC
              (SEQ ID NO. 3)
asp-VT2-2b    GAACGTTCCACCGCTGCGACA
              (SEQ ID NO. 4)
```

Figure 4:
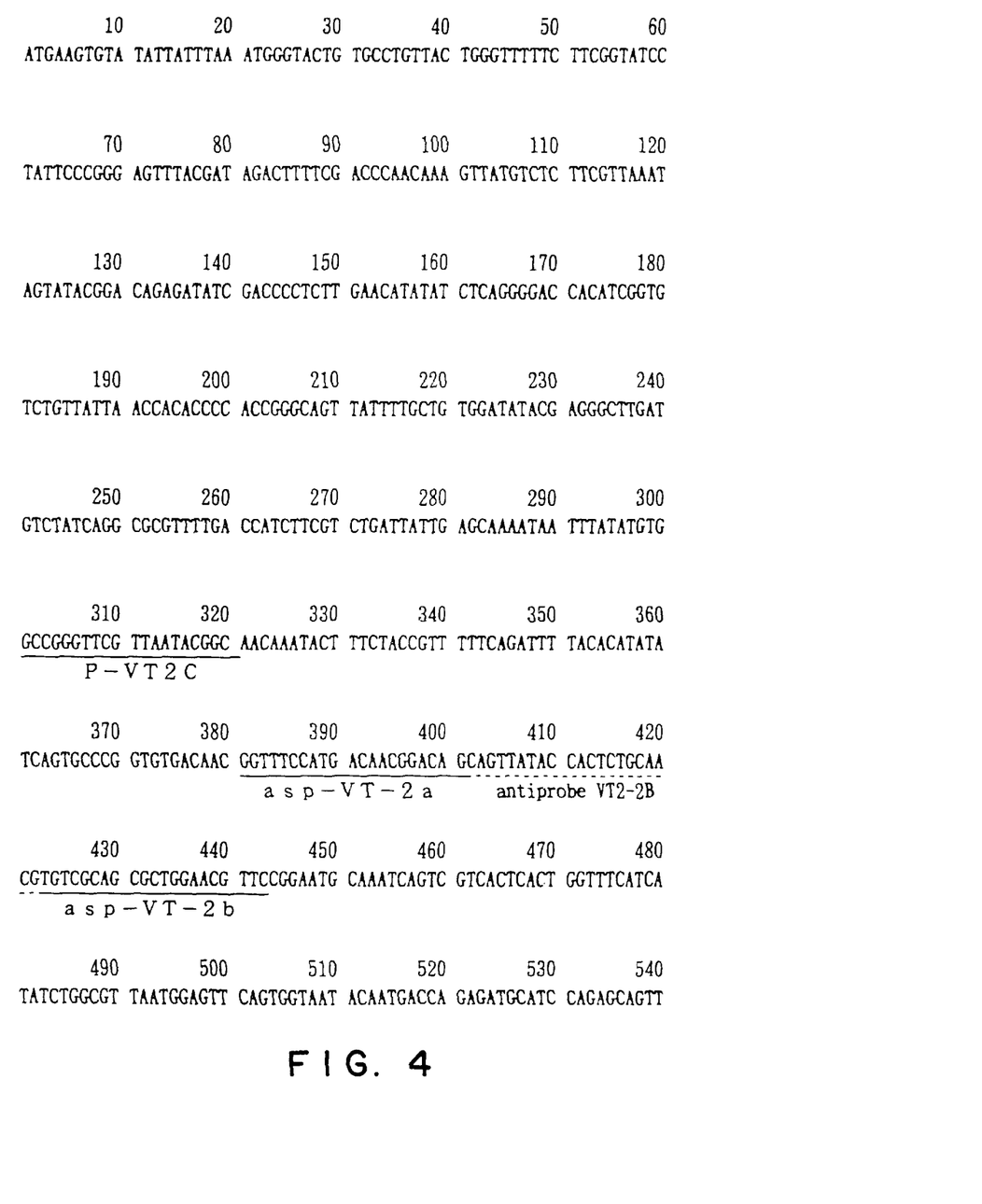
FIG. 4 shows a DNA sequence coding for Type II verotoxin of pathogenic *Escherichia coli* O-157 (SEQ ID NO:1).

P-VT2C, asp-VT2-2a and asp-VT2-2b correspond to the base sequences 301–321, 381–401 and 423–443 of the DNA sequence shown in FIG. 4, respectively.

An asymmetric PCR was performed using a genome DNA extracted from pathogenic *E. coli* O-157 as a template and P-VT2C and asp-VT2-2b as primers. P-VT2C and asp-VT2-2b were added in a 20:1 ratio. After an initial denaturation (94° C., 3 minutes), the PCR was performed for 10 to 40 cycles of denaturation (94° C., 1 minute), annealing (59° C., 5 minutes) and elongation (72° C., 1 minute).

An asymmetric PCR was also performed using P-VT2C and asp-VT2-2a as primers as described above. asp-VT2-2b and P-VT2C were added in a 20:1 ratio.

Figure 5:
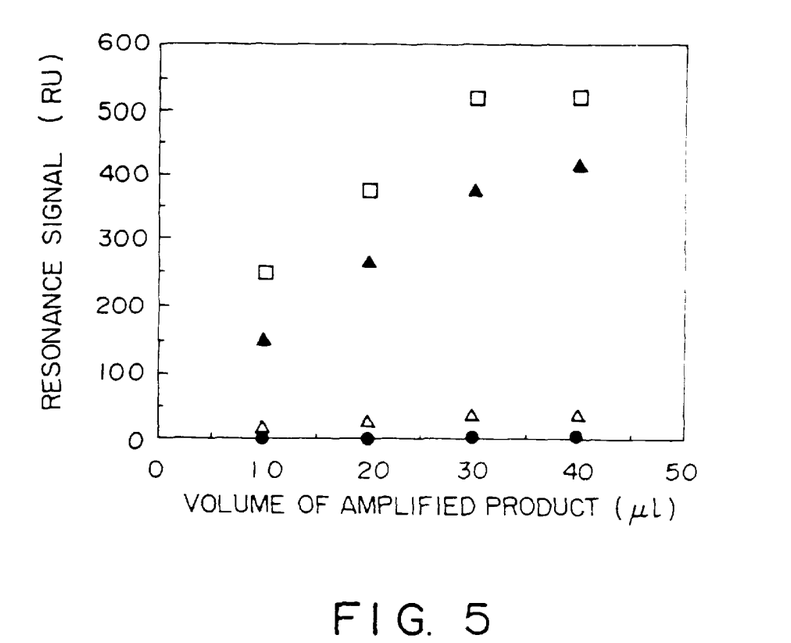
FIG. 5 shows the relationship between a PCR cycle and resonance signals when a partially double-stranded nucleotide sequence was used.

Two kinds of PCR amplification products obtained as described above were mixed to a total volume of 100 μl. The mixture was heated at 95° C. for 10 minutes and then cooled to 25° C. for 30 minutes to produce a partially double-stranded DNA. The mixture of amplification products containing this partially double-stranded DNA was poured into the measuring cell of the abovementioned biosensor and resonance signals were measured at flow volumes of 10 μl, 20 μl, 30 μl and 40 μl. Results are shown in FIG. 5. For a control, a PCR (symmetric PCR) was performed using P-VT2C and asp-VT2-2b as primers and the resulting amplification product was poured into the measuring cell to measure resonance signals. Results are shown in FIG. 6. ○: 10 cycles, ●: 20 cycles, Δ: 25 cycles, ▲: 30 cycles and □: 40 cycles.

Figure 6:
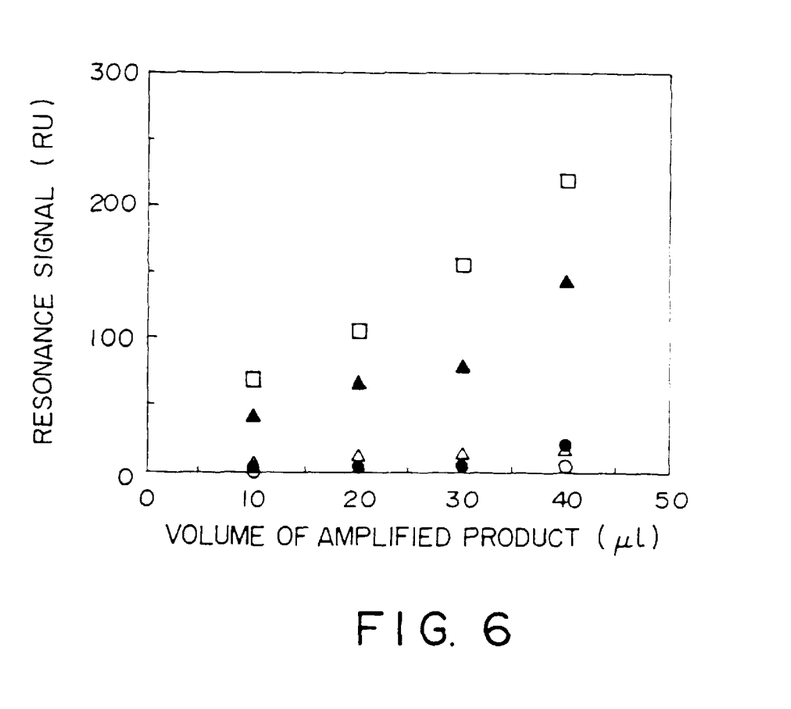
FIG. 6 shows the relationship between a PCR cycle and resonance signals when a partially double-stranded nucleotide sequence was not used.

As shown in FIGS. 5 and 6, hybridization signals could be detected for 30 and more cycles in both cases. Moreover, detection sensitivity was improved about two times by making the asymmetric PCR products into the partially double-stranded DNA.

Example 2

An asymmetric PCR was performed using a genome DNA extracted from pathogenic *E. coli* O-157 as a template and P-VT2C and asp-VT2-2b as primers (the resulting amplification product is referred to as "amplification product A"). P-VT2C and asp-VT2-2b were added in a 20:1 ratio. After an initial denaturation (95° C., 3 minutes), PCR was performed for 40 cycles of denaturation (94° C., 1 minute), annealing (61° C., 1 minute) and elongation (72° C., 1 minute).

An asymmetric PCR was performed using a genome DNA extracted from pathogenic *E. coli* O-157 as a template and P-VT2C and asp-VT2-2a as primers (the resulting amplification product is "amplification product B"). asp-VT2-2a and P-VT2C were added in a 20:1 ratio. The PCR was performed under the same conditions as described above.

A asymmetric PCR was performed using a genome DNA extracted from pathogenic *E. coli* O-157 as a template and P-VT2C and asp-VT2-2b as primers (the resulting amplification product is "amplification product C"). The PCR was performed under the same conditions as described above.

A symmetric PCR was performed using a genome DNA extracted from pathogenic *E. coli* O-157 as a template and P-VT2C and asp-VT2-2a as primers (the resulting amplification product is "amplification product D"). The PCR was performed under the same conditions as described above.

The amplification products A, B, C and D were mixed in four combinations: ①  amplification product C+amplification product D, ②  amplification product A+amplification product B, ③  amplification product A+amplification product D and ④  amplification product B+amplification product C. These mixed amplification products were heated at 95° C. for 10 minutes and then cooled to 25° C. for 30 minutes. These four kinds of mixed amplification products were poured into measuring cells of the biosensor and resonance signals were measured at flow volumes of 10 μl, 20 μl, 30 μl and 40 μl. Results are shown in FIG. 7. ○: mixed amplification product ①, ●: mixed amplification product ②, Δ: mixed amplification product ③ and ▲: mixed amplification product ④.

Figure 7:
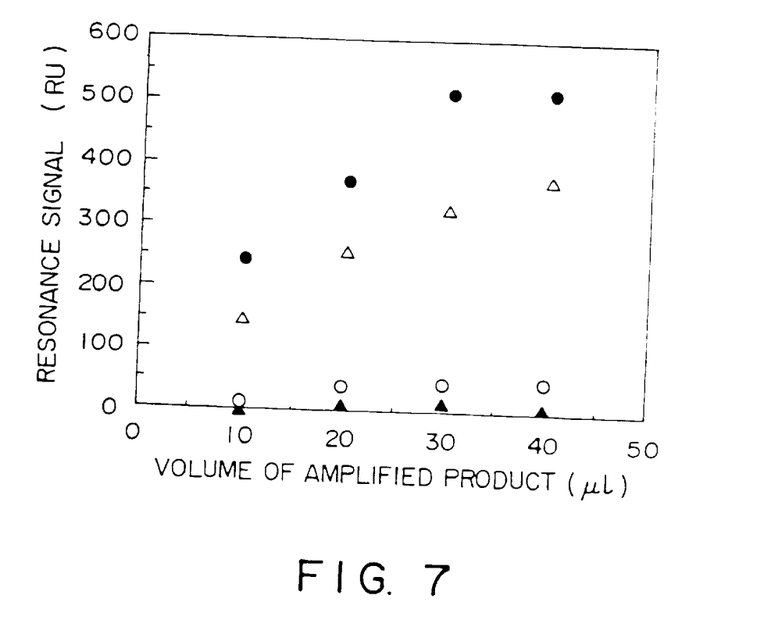
FIG. 7 shows the relationship between a structure of an amplification product and resonance signals.

As shown in FIG. 7, the sensitivity of detection was best when two asymmetric PCR amplification products were mixed (mixed amplification product ②).

Example 3

A mixed amplification product of amplification product A and amplification product B prepared in Example 2 was heated at 95° C. for 10 minutes and then cooled to 25° C. for 30 minutes to produce a partially double-stranded DNA. The mixed amplification product containing this partly double-stranded DNA was poured into a measuring cell of the biosensor and resonance signals were measured at flow volumes of 10 μl, 20 μl, 30 μl and 40 μl. Amplification product A alone was heated and cooled to prepare a sample for control 1, a mixture of amplification product A and amplification product B was heated and cooled to prepare a sample for control 2, amplification product A alone was heated but not cooled to prepare a sample for control 3. Resonance signals were measured for these control samples in the same manner as described above. Results are shown in FIG. 8. ○: the sample containing the partially double-stranded DNA, ●: control 1, Δ: control 2 and ▲: control 3.

Figure 8:
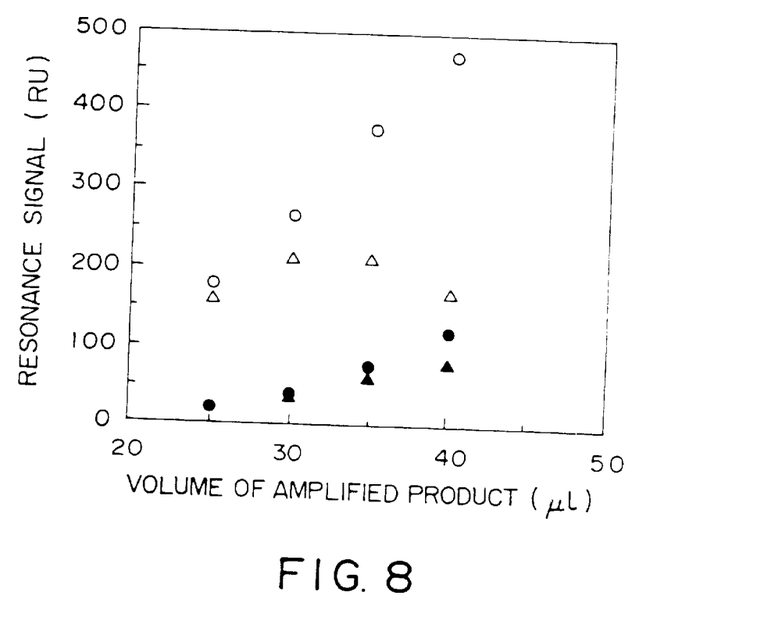
FIG. 8 shows the relationship between the presence and absence of a heating process and resonance signals after the admixing of the amplification product.

As shown in FIG. 8, a significant signal was not detected for samples comprising amplification product A alone. Furthermore, certain signals were always detectable for these samples comprised of mixed amplification products. However, the sensitivity of detection was definitely poor when heating and cooling processes were not applied.

Example 4

A layer chrome and then a gold layer were deposited on a 13 mm×18 mm and 0.3 mm thick blue glass plate (Matsunami Glass Kogyo) by sputtering to produce a measuring chip for a surface plasmon resonance biosensor. Sputtering was carried out at 100 W for 30 seconds to produce a 32.2 angstrom chrome layer; and at 100 W for 150 seconds to produce a 474 angstrom gold layer. This measuring chip was immersed into a 1 mM ethanol solution of 11-mercaptoundecanoic acid for 24 hours to form a thin organic membrane layer on the metal layer. Then, 50 μl of a 5% avidin solution were dropped at 3 spots on the same chip, wherein amides bonds were formed between the avidin molecules and the thin organic membrane molecules, thus immobilizing the avidin molecules.

The following three kinds of DNA with biotin bonded at the 5' end (synthesized by Sawaday Technology). These DNAs have sequences complementary to a part of three kinds of genes, tdh1, tdh2 and trh2, which are the toxic elements of a toxin producing bacteria, *Vibrio parahaemolyticus*.

| | |
|---|---|
| Sequence A (tdh1): AAGTTATTAATCAAT | (SEQ ID NO. 5) |
| Sequence B (tdh2): TTTTTATTATATCCG | (SEQ ID NO. 6) |
| Sequence C (trh2): CCCAGTTAAGGCAAT | (SEQ ID NO. 7) |

30 μl of a solution containing the abovementioned DNA (10 μl) were dropped onto the spots where the avidin solution was dropped to immobilize the DNA onto the measuring chip via an avidin-biotin bond.

Figure 9:
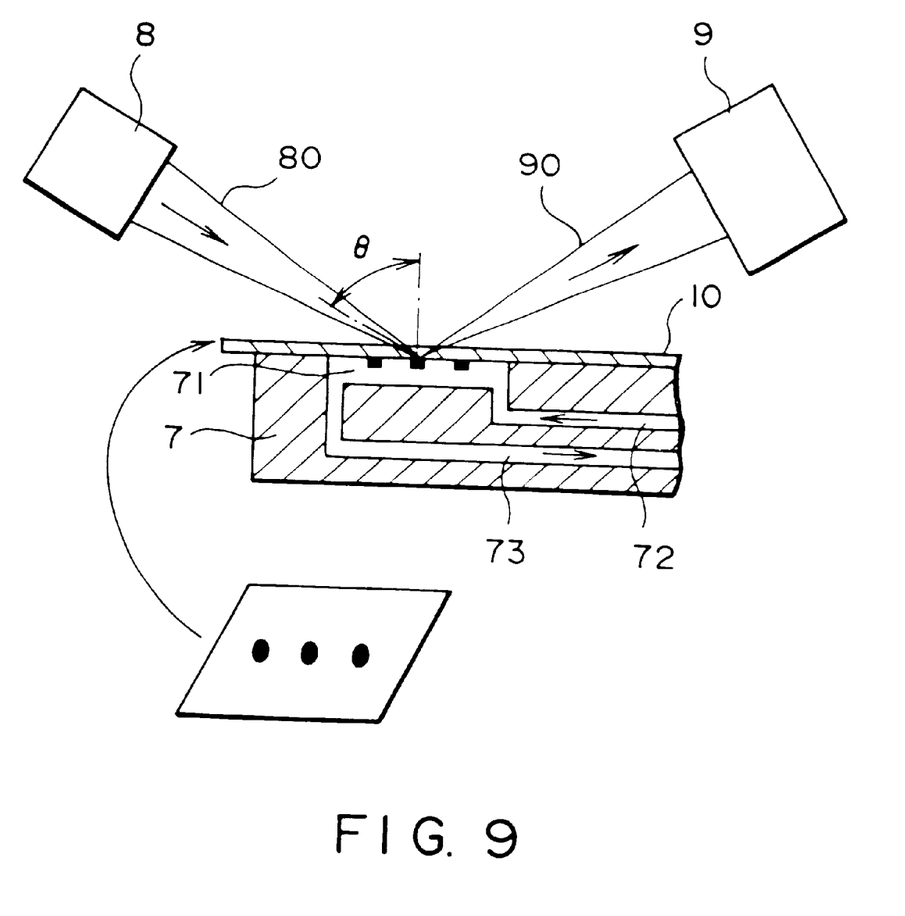
FIG. 9 shows a typical embodiment of the surface plasmon resonance biosensor used in the detection method according to the present invention. Symbols used in FIG. 9 are the same as defined in FIG. 2.

The measuring chip on which the DNA was immobilized was placed onto a surface plasmon resonance biosensor (SPR-20 type with a modified sensor head and fluid supply and drainage, Denki Kagaku Keiki) (FIG. 9). Since the measuring chip of this biosensor can freely move horizontally, resonance signals of the multiple numbers of samples present on the chip can be measured leaving the optical system fixed.

The DNA sequence to be detected was amplified as a partially double-bonded DNA (143 bp for the double-stranded DNA and 101 bp for the single-stranded DNA) using an asymmetric PCR as described in Example 1. A solution containing the amplified partially double-stranded DNA was poured into a measuring cell of the biosensor to measure resonance signals at a flow volume of 10 μl. Results are shown in Table 1.

TABLE 1

| Sequence | A | B | C |
|---|---|---|---|
| Resonance signal ($\times 10^{-4°}$) | 308 (RU) | 298 (RU) | 315 (RU) |

As shown in Table 1, sequences A, B and C all show signals near 300 RU (converted values). Considering the fact that the signals are 10–20 RU (converted values) when no DNA is bound (negative), then it would appear that the partially double-stranded DNA was bound to the three kinds of immobilized DNAs (positive).

Example 5

A metal layer and a thin organic membrane layer were deposited on a blue plate glass and four measuring chips were prepared as described in Example 4. 50 μl of a 5% avidin solution were dropped on two spots each of the four chips (totally 8 spots) to immobilize the avidin molecules.

The following 8 DNAs to which biotin is bound at their 5' ends were synthesized (synthesized by Sawaday Technology). Sequences A, B and C are DNAs which have sequences complementary to a part of gene tdh1, tdh2 and trh2 of *Vibrio parahaemolyticus*, respectively. Sequences D, E, F, G and H are DNAs which have sequences complementary to 18S rRNA of *Salmonella enteritidis*, a pertussis toxin of *Borderlia pertussis*, *Vibrio cholera* toxin, type I verotoxin of *Escherichia coli* O-157 (pathogenic *E. coli* O-157) and type II verotoxin of *E. coli* O-157, respectively.

| | |
|---|---|
| Sequence A: AAGTTATTAATCAAT | (SEQ ID NO. 5) |
| Sequence B: TTTTTATTATATCCG | (SEQ ID NO. 6) |
| Sequence C: CCCAGTTAAGGCAAT | (SEQ ID NO. 7) |
| Sequence D: CGCAAACCGTATTAC | (SEQ ID NO. 8) |
| Sequence E: CCAAAGTATTTCCCT | (SEQ ID NO. 9) |
| Sequence F: AATTCGGGTTAATTG | (SEQ ID NO. 10) |
| Sequence G: GGGCGTTATGCCGTA | (SEQ ID NO. 11) |
| Sequence H: TGCAGAGTGGTATAA | (SEQ ID NO. 12) |

30 μl of a solution containing the DNA (10 μl) were dropped onto the spots where the avidin solution was dropped to immobilize the DNA onto the measuring chip via avidin-biotin bonds.

The measuring chip on which the DNA was immobilized was placed onto the surface plasmon resonance biosensor used in Example 4. The DNA to be detected was amplified as a partially double-bonded DNA (143 bp for the double-stranded DNA and 101 bp for the single-stranded DNA) using the asymmetric PCR as described in Example 4. Four DNAs were used; DNAs prepared from *E. coli* O-157, *Vibrio parahaemolyticus*, and Salmonella and a combination of DNAs from *E. coli* O-157 and Salmonella. A solution containing the amplified partially double-stranded DNA was poured into a measuring cell of the biosensor to measure resonance signals at a flow volume of 10 μl. Results are shown in Table 2.

TABLE 2

| | *E. coli* O-157 | *V. parahaemoliticus* | Salmonella | *E. coli* O-157 + Salmonella |
|---|---|---|---|---|
| Sequence A | 22 | 295 | 10 | 11 |
| Sequence B | 18 | 331 | 12 | 28 |
| Sequence C | 21 | 301 | 18 | 23 |
| Sequence D | 15 | 22 | 321 | 299 |
| Sequence E | 17 | 24 | 22 | 18 |
| Sequence F | 24 | 19 | 33 | 19 |
| Sequence G | 308 | 18 | 24 | 356 |
| Sequence H | 311 | 25 | 26 | 334 |

As shown in Table 2, for the various microorganisms, signals near 300 RU were obtained for positive samples and signals less than 30 RU were obtained for negative samples.

What is claimed is:

1. A method for detecting a target nucleotide sequence that comprises:

converting a target nucleotide sequence to a partially double-stranded nucleotide sequence which has a double-stranded part and a single-stranded part; and detecting the partially double-stranded nucleotide sequence using a nucleotide sequence that is complementary to the target nucleotide sequence, wherein converting the target nucleotide sequence into the partially double-stranded nucleotide sequence includes:

(1) performing an asymmetric polymerase chain reaction in which a target nucleotide sequence is used as a template and an oligonucleotide having a nucleotide sequence identical to a part of the target nucleotide sequence (primer 1) and an oligonucleotide having a nucleotide sequence complementary to a part of the target nucleotide sequence (primer 2) are used as primers;

(2) performing an asymmetric polymerase chain reaction in which the target nucleotide sequence is used as a template and primer 1 and an oligonucleotide having a nucleotide sequence complementary to a part of the target nucleotide sequence except for primer 2 (primer 3) are used as primers; and (3) obtaining a partially double-stranded nucleotide sequence by heating and cooling a mixture of the amplification products of (1) and (2).

2. A method according to claim 1 wherein the nucleotide sequence that is complementary to the target nucleotide sequence is a nucleotide sequence complementary to the single-stranded part of the partially double-stranded nucleotide sequence or a portion thereof.

3. A method according to claim 1 wherein primers 2 and 3 each consist of a part of a nucleotide sequence which is complementary to the target nucleotide sequence and located downstream from the position of primer 1 on the target nucleotide sequence.

4. A method according to claim 1 wherein primers 2 and 3 each consist of a part of a nucleotide sequence which is complementary to the target nucleotide sequence and located downstream from the position of primer 1 on the target nucleotide sequence and wherein primer 2 consists of a part of a nucleotide sequence which is complementary to the target nucleotide sequence and located downstream from the position of a nucleotide sequence complementary to primer 3 on the target nucleotide sequence.

5. A method according to claim 1 wherein primer 1 is provided in excess over primer 2 in (1) and primer 3 is provided in excess over primer 1.

6. A method according to claim 1 wherein the ratio of primer 1 to primer 2 and the ratio of primer 3 to primer 1 present is 10 to 100.

7. A method according to claim 1 which further comprises prior to (1):

(A) synthesizing an oligonucleotide (primer 1) having a nucleotide sequence identical to a part of the target nucleotide sequence; and (B) synthesizing two oligonucleotides (primer 2 and primer 3) having a nucleotide sequence complementary to a part of the target nucleotide sequence.

8. A method according to claim 1 wherein the double-stranded part is 100 to 2000 base pairs and the single-stranded part is 85 to 1985 base pairs.

9. A method according to claim 1 wherein the partially double-stranded nucleotide sequence is detected by a surface plasmon resonance biosensor.

10. A method according to claim 1 wherein the nucleotide sequence complementary to the target nucleotide sequence is immobilized on a measuring chip of a surface plasmon resonance biosensor.

11. A method according to claim 1 wherein two or more target nucleotide sequences are detected.

12. A method according to claim 1 wherein the nucleotide sequence is DNA.

13. A method for producing a partially double-stranded nucleotide sequence, comprising:

(1) performing an asymmetric polymerase chain reaction in which a target nucleotide sequence is used as a template and an oligonucleotide having a nucleotide sequence identical to a part of the target nucleotide sequence (primer 1) and an oligonucleotide having a nucleotide sequence complementary to a part of the target nucleotide sequence (primer 2) are used as primers;

(2) performing an asymmetric polymerase chain reaction in which the target nucleotide sequence is used as a template and primer 1 and an oligonucleotide having a nucleotide sequence complementary to a part of the target nucleotide sequence except for primer 2 (primer 3) are used as primers; and (3) obtaining a partially double-stranded nucleotide sequence by heating and cooling a mixture of the amplification products of (1) and (2).

* * * * *

SEQUENCE LISTING

<160> NUMBER OF SEQ ID NOS: 12

<210> SEQ ID NO 1
<211> LENGTH: 540
<212> TYPE: DNA
<213> ORGANISM: Escherichia coli -continued

```
<400> SEQUENCE: 1
atgaagtgta tattatttaa atgggtactg tgcctgttac tgggttttc tcggtatcc       60 tattcccggg agtttacgat agacttttcg acccaacaaa gttatgtctc tcgttaaat    120 agtatacgga cagagatatc gacccctctt gaacatatat ctcagggac  acatcggtg    180 tctgttatta accacacccc accgggcagt tattttgctg tggatatacg a gggcttgat   240 gtctatcagg cgcgttttga ccatcttcgt ctgattattg agcaaaataa t ttatatgtg   300 gccgggttcg ttaatacggc aacaaatact ttctaccgtt tttcagattt t acacatata   360 tcagtgcccg gtgtgacaac ggtttccatg acaacggaca gcagttatac c actctgcaa   420 cgtgtcgcag cgctggaacg ttccggaatg caaatcagtc gtcactcact g gtttcatca   480 tatctggcgt taatggagtt cagtggtaat acaatgacca gagatgcatc c agagcagtt   540
```

```
<210> SEQ ID NO 2
<211> LENGTH: 21
<212> TYPE: DNA
<213> ORGANISM: Artificial Sequence
<220> FEATURE:
<223> OTHER INFORMATION: Description of Artificial  Sequence:Synthetic
                        DNA

<400> SEQUENCE: 2
gccgggttcg ttaatacggc a                                                21
```

```
<210> SEQ ID NO 3
<211> LENGTH: 21
<212> TYPE: DNA
<213> ORGANISM: Artificial Sequence
<220> FEATURE:
<223> OTHER INFORMATION: Description of Artificial  Sequence:Synthetic
                        DNA

<400> SEQUENCE: 3
ctgtccgttg tcatggaaac c                                                21
```

```
<210> SEQ ID NO 4
<211> LENGTH: 21
<212> TYPE: DNA
<213> ORGANISM: Artificial Sequence
<220> FEATURE:
<223> OTHER INFORMATION: Description of Artificial  Sequence:Synthetic
                        DNA

<400> SEQUENCE: 4
gaacgttcca gcgctgcgac a                                                21
```

```
<210> SEQ ID NO 5
<211> LENGTH: 15
<212> TYPE: DNA
<213> ORGANISM: Artificial Sequence
<220> FEATURE:
<223> OTHER INFORMATION: Description of Artificial  Sequence:Synthetic
                        DNA

<400> SEQUENCE: 5
aagttattaa tcaat                                                       15
```

```
<210> SEQ ID NO 6
<211> LENGTH: 15
<212> TYPE: DNA
<213> ORGANISM: Artificial Sequence
<220> FEATURE:
```

```
<223> OTHER INFORMATION: Description of Artificial  Sequence:Synthetic
                                DNA

<400> SEQUENCE: 6
tttttattat atccg                                                    15

<210> SEQ ID NO 7
<211> LENGTH: 15
<212> TYPE: DNA
<213> ORGANISM: Artificial Sequence
<220> FEATURE:
<223> OTHER INFORMATION: Description of Artificial  Sequence:Synthetic
                                DNA

<400> SEQUENCE: 7
cccagttaag gcaat                                                    15

<210> SEQ ID NO 8
<211> LENGTH: 15
<212> TYPE: DNA
<213> ORGANISM: Artificial Sequence
<220> FEATURE:
<223> OTHER INFORMATION: Description of Artificial  Sequence:Synthetic
                                DNA

<400> SEQUENCE: 8
cgcaaaccgt attac                                                    15

<210> SEQ ID NO 9
<211> LENGTH: 15
<212> TYPE: DNA
<213> ORGANISM: Artificial Sequence
<220> FEATURE:
<223> OTHER INFORMATION: Description of Artificial  Sequence:Synthetic
                                DNA

<400> SEQUENCE: 9
ccaaagtatt tccct                                                    15

<210> SEQ ID NO 10
<211> LENGTH: 15
<212> TYPE: DNA
<213> ORGANISM: Artificial Sequence
<220> FEATURE:
<223> OTHER INFORMATION: Description of Artificial  Sequence:Synthetic
                                DNA

<400> SEQUENCE: 10
aattcgggtt aattg                                                    15

<210> SEQ ID NO 11
<211> LENGTH: 15
<212> TYPE: DNA
<213> ORGANISM: Artificial Sequence
<220> FEATURE:
<223> OTHER INFORMATION: Description of Artificial  Sequence:Synthetic
                                DNA

<400> SEQUENCE: 11
gggcgttatg ccgta                                                    15

<210> SEQ ID NO 12
<211> LENGTH: 15
<212> TYPE: DNA
<213> ORGANISM: Artificial Sequence
<220> FEATURE:
```

-continued

```
<223> OTHER INFORMATION: Description of Artificial  Sequence:Synthetic
                        DNA

<400> SEQUENCE: 12
tgcagagtgg tataa                                                  15
```